United States Patent
Boren

(10) Patent No.: US 8,088,205 B2
(45) Date of Patent: Jan. 3, 2012

(54) WOOD PRESERVATIVE AND METHOD FOR MANUFACTURING WOOD PRESERVATIVE

(75) Inventor: Hannu Boren, Kohtavaara (FI)

(73) Assignee: Holjakka Oy, Joensuu (FI)

( * ) Notice: Subject to any disclaimer, the term of this patent is extended or adjusted under 35 U.S.C. 154(b) by 0 days.

(21) Appl. No.: 12/308,638

(22) PCT Filed: Aug. 7, 2007

(86) PCT No.: PCT/FI2007/000198
§ 371 (c)(1),
(2), (4) Date: Dec. 18, 2008

(87) PCT Pub. No.: WO2008/017730
PCT Pub. Date: Feb. 14, 2008

(65) Prior Publication Data
US 2010/0263570 A1    Oct. 21, 2010

(30) Foreign Application Priority Data

Aug. 9, 2006   (FI) ..................................... 20060718

(51) Int. Cl.
*A01N 61/00* (2006.01)
*B27K 3/50* (2006.01)
*B27K 3/52* (2006.01)
*C09D 15/00* (2006.01)
*C11B 13/00* (2006.01)

(52) U.S. Cl. ........... 106/17; 106/15.05; 106/16; 106/18; 252/397; 252/398; 252/404; 252/407; 514/782; 514/783; 514/784

(58) Field of Classification Search ............... 106/15.05, 106/16, 17, 18; 252/397, 398, 404, 407; 514/782, 783, 784
See application file for complete search history.

(56) References Cited

U.S. PATENT DOCUMENTS

| 2005/0186352 A1 | 8/2005 | Hutter et al. ............... 427/430.1 |
| 2007/0087213 A1* | 4/2007 | Robinson et al. ............ 428/541 |
| 2009/0117400 A1* | 5/2009 | Boren ........................ 428/537.1 |

FOREIGN PATENT DOCUMENTS

| EP | 1 568 760 A1 | 8/2005 |
| EP | 1 586 624 A1 | 10/2005 |
| FI | 97707 B | 10/1994 |
| FI | 114920 B | 3/2004 |
| SE | 520123 C2 | 3/2003 |
| WO | WO-03/024681 A1 | 3/2003 |

OTHER PUBLICATIONS

"Wood Chemistry, Fundamentals and Applications—Chapter 10, Chemicals from Wood and By-Proudcts after Pulping", Eero Sjostrom, Academic Press Inc., London, UK 1981, 5 pgs.

* cited by examiner

*Primary Examiner* — Anthony J Green

(74) *Attorney, Agent, or Firm* — Harrington & Smith

(57) ABSTRACT

The invention relates to a wood preservative, which wood preservative contains vegetable oils processed from crude tall oil, such as resin acids and fatty acids. The wood preservative according to the invention is characterized by that the wood preservative is crude tall oil, from which have been removed neutral components contained by the crude tall oil, especially compounds acting as the breeding ground and nutriment of rot fungi and/or compounds causing esterification reactions, such as fatty alcohols and/or steroid groups, such as sitosterol and sitostanol. The invention also relates to a method for manufacturing wood preservative according to the invention.

8 Claims, No Drawings

WOOD PRESERVATIVE AND METHOD FOR MANUFACTURING WOOD PRESERVATIVE

The invention relates to a wood preservative, which wood preservative contains vegetable oils processed from crude tall oil, such as resin acids and fatty acids. The invention also relates to a method for manufacturing wood preservative, in which method, wood preservative is manufactured from vegetable oils, such as fatty acids and resin acids, contained by crude tall oil.

Wood preservatives try to prevent or decelerate the actions of fungoid growths, such as brown, white and soft rot fungi, which chemically rot wood. Most effectively, wood is protected by pressure-impregnating the wood with a preservative until heartwood. The wood preservatives most commonly used recently in pressure impregnation can mainly be divided into three classes: 1. water-based impregnants, 2. oil-based impregnants, and 3. creosote oil. Furthermore, recently wood has been preserved by treating the wood with crude tall oil or mixtures of resin and fatty acids processed from it. For example, Finnish specification FI97707 describes a wood preservation method and a wood preservative based on the use of crude tall oil.

A disadvantage of traditional water- and oil-based impregnants and creosote oil is their general toxicity to all living organisms. Because of this, their use involves considerable risks to health and the environment. A disadvantage of crude tall oil or wood preservatives processed from it has been their low rot preservation capability especially if an adequate amount of preservative has not been obtained inside wood. In addition, a disadvantage of crude tall oil is its bad odour which is caused by the use of sulphuric acid in the acid treatment. A further problem of crude tall oil and wood preservatives processed from it is that, after pressure impregnation treatment, wood preservative seeps onto the surface of wood, because there has to be a relatively large amount of wood preservative inside the wood for achieving an adequate protective effect. Furthermore, a disadvantage of recently known wood preservatives manufactured by mixing vegetable oils processed from crude tall oil, such as industrially manufactured resin and fatty acids, is the complexity and expensiveness of the manufacturing process due to multistage distillation or extraction processes required by them and the weakening of oil characteristics from the viewpoint of wood preservation.

An object of the invention is to provide a wood preservative by means of which above-mentioned problems related to recently known wood preservatives are eliminated. Especially, an object of the invention is to introduce a wood preservative based on crude tall oil which is not harmful to human health and the environment but, by means of which, wood or wood products manufactured of it are protected from strains of weather, decay and moulding better than earlier. Furthermore, an object of the invention is to introduce a method for manufacturing wood preservative which method is simpler and more cost-effective than the earlier manufacturing methods of wood preservatives based on vegetable oils derived from crude tall oil and, by means of which method, the consistency of the oil is better from the viewpoint of wood preservation.

The object of the invention is achieved with a wood preservative and a method for manufacturing wood preservative which are characterised by what is presented in the claims.

The wood preservative according to the invention is characterised by that the wood preservative is manufactured of crude tall oil by removing neutral components from the crude tall oil, from which are especially removed compounds acting as the breeding ground and nutriment of rot fungi and compounds increasing esterification, such as steroids, of which especially sitosterols and sitostanols, and/or fatty alcohols. Rot resistance tests and studies made with crude tall oil have proved that with a mixture of resin and fatty acids originating from crude tall oil is obtained the best effect in preventing wood decay. Additionally, latest studies have shown that part of neutral components contained by crude tall oil weaken the rot-resistance-increasing effects of crude tall oil. The weakening effect of these components is based on that they offer rot fungi a good breeding ground i.e. they act as a nutrient source for the rot fungi. Even though part of neutral components have an effect weakening the growth of rot fungi according to studies, they still occur in oil in such small contents that the advantages provided by them are smaller than the disadvantages of components acting as the breeding ground. When esterified, these components also release water in the wood which is a prerequisite for the growth of rot fungi. Furthermore, esterifying reactions consume acid components important from the viewpoint of wood preservation from the oil. By minimising the share of components suitable to be the nutrient of rot fungi in the oil and by simultaneously decreasing esterification, the subsistence of the rot fungi is minimised in the wood treated with oil. Because of this, better protection from rot is obtained with such a wood preservative, which is formed of crude tall oil so that neutral components are removed from the crude tall oil, than with unprocessed crude tall oil and such known crude tall oil in which resin acids, fatty acids or fatty-acid-bearing crude tall oil (e.g. crude tall oil obtained from birch) have been inserted. Additionally, it is difficult to manufacture totally pure resin acids and fatty acids and they are extremely expensive because they are the raw material of, inter alia, paints and glues. Because of this, oil of better quality and cheaper price is obtained in connection with boiling chemical pulp by removing neutral components at the starting stage. The pure distillation of neutral components out from crude tall oil later is also a more inexpensive way to operate than to add pure resin acids and/or fatty acids in crude tall oil. The more neutral components are removed and the more accurately the removal can be focused on compounds acting as nutriment and compound groups increasing esterification, such as fatty alcohols, the better oil is obtained from the viewpoint of protecting wood from rot.

The neutral components of crude tall oil contain many different compound groups, worth mentioning e.g. terpenes/terpenoids consisting of isoprene units (C5). Terpene groups are e.g. monoterpenes, sesquiterpenes, diterpenes, triterpenes, tetraterpenes and polyterpenes. Monoterpenes consist of two isoprene units (C10) and their share of neutral components is e.g. about 0-5%. An example of a compound in the monoterpene group is isoborneol. As an example of sesquiterpenes (0-5%), which consist of three isoprene units (C15), can be mentioned longifolene. Diterpenes (0-5%) consist of four isoprene units. The diterpene group includes, inter alia, sembrene and pimaradiene. Triterpenes (0-3%) consist of six isoprene units. The neutral components contained by crude tall oil also include resin alcohols (10-60%), e.g. pimarinol, sandaracopimarinol, isopimarinol, larixol and elliotienol, and resin aldehydes (0-6%), inter alia, pimarinal and isopimarinal, to mention a few. An important neutral component group from the viewpoint of wood protection is steroids (10-60%). Steroids, which are tetracyclic compounds, are e.g. β-sitosterol (5-40%), β-sitostanol (2-10%) and cycloartenol (0-6%). The neutral component groups of crude tall oil are also fatty alcohols (3-20%), e.g. tetracosanol and docosanol, and phenols (0-3%), examples of which are phenol, 2-methylphenol and 4-clorophenol. Also stilbenes (0-2%) are included in the neutral components. The relative amounts of neutral components included in crude tall oil vary a lot depending on the origin of the crude tall oil.

The removal of neutral components can be done, if desired, selectively so that a part of neutral components naturally protecting wood is left to the oil. Such components are e.g. monoterpenes and phenols. The removal of neutral components concentrates especially on the compounds of the steroid group. Steroids, of which are mentioned sitosterol and sitostanol, are classified as fats and their disintegration products e.g. through oxidation can impede the wood preserving characteristics of crude tall oil.

In an embodiment of wood preservative according to the invention, neutral components have been removed by extracting. The advantage of extraction is that, by means of it, the content of neutral components is obtained extremely small relatively easy. Extracting takes place most advantageously in connection with boiling chemical pulp.

In an embodiment of wood preservative according to the invention, neutral components have been removed by distilling. The advantage of distillation is that the saponification stages of crude tall oil required in extraction and the restoration of the solution back to tall oil are avoided.

In an embodiment of wood preservative according to the invention, components contributing to esterification have been removed and the treatment temperatures and times of crude tall oil for minimising the esterification reactions of the wood preservative have been diminished.

The method according to the invention is characterised by that wood preservative is manufactured of crude tall oil by removing neutral components from the crude tall oil, especially compounds causing esterification reactions and/or compounds acting as the breeding ground and nutriment of rot fungi, such as fatty alcohols, and/or steroids, such as sitosterol and sitostanol. Such a manufacturing method does not require so many extraction or distillation stages as the manufacturing of wood preservatives manufactured with recently known ways based on the resin and/or fatty acids of crude tall oil. Many times, only one or two extraction/distillation stages are required. Because of this, such a manufacturing method of wood preservative based on crude tall oil is clearly simpler and more cost-effective than earlier. Furthermore, useful components contained by crude tall oil, such as phenols and mono- and diterpenes and neutral components useful from the viewpoint of wood preservation, can be left in the wood preservative.

The invention will now be described in more details by means of a few embodiments as examples.

When manufacturing a wood preservative according to the invention, neutral components contained by crude tall oil are removed from crude tall oil by extracting. Then, in the remaining solution there are advantageously 60 wt % of fatty acids, 38 wt % of resin acids and about 2 wt % of remaining neutral components.

The extracting of neutral components from crude tall oil comprises three stages: 1. saponification stage, 2. extraction stage, and 3. acidifying i.e. restoring to tall oil.

Saponification takes place by boiling crude tall oil e.g. in KOH or NaOH solutions. Other possible alkalis used in boiling are e.g. LiOH and RbOH. The alkalis are used as aqueous solutions of desired concentration. The content of alkali is usually defined in relation to the saponification value of crude tall oil which value can be e.g. 1.0-3.0× saponification value of tall oil, suitably 1.0-1.5× saponification value of tall oil. The more alkali is used, the shorter the boiling time in saponification is. The saponification times are usually 30-240 min and the saponification temperatures e.g. between 30-200° C. The best results are usually achieved with a boiling temperature which varies between 110-120° C. The suitable pressure varies between 1-15 atm.

A suitable saponification solution is e.g. a water/alcohol solution in the ratio of 1:1-1:2. A suitable ratio of saponification solution to tall oil is 1:1-1:2, because then it is possible to use higher temperatures and blendability remains good. It is also possible to use a sole water/alkali solution. Water acts e.g. as a solvent of alkali and a phase for saponifiable fatty and resin acids. Alcohol decreases foaming and accelerates the reaction of tall oil with alkali (dispersation), whereby the building of soap is quicker. The saponifiable crude tall oil (the salts of resin acids and fatty acids) constitutes its own phase ("water phase") and the unsaponifiable neutral components their own phase ("organic phase").

Extracting can be done as a batch process or, in continuous systems, either in one or more stages in apparatuses which can comprise stirred tank reactors, packed columns or centrifuges. In manufacturing wood preservative according to the invention, usually one or two extraction stages are adequate.

For extracting, e.g. a mixture of polar and nonpolar solvents can be used. There are several different alternatives with these. Viable extraction solvents are aromatic organic solutions, such as benzene and toluene, and aliphatic i.e. straight-chain hydrocarbons, such as diethyl ether, hexane, heptane, octane, xylene, decane, cyclohexane, isopropyl alcohol, naphtha, dialkylated ketones, acetyl esters, acetone and petroleum ether. Of these, hexane is one of the best, inter alia, because of its cheap price.

A problem of extraction has been separating soap from the mixture (creating stable emulsion) and the foaming of the solution during extraction. The problem can be minimised by using in the extracting nonpolar solvent and soap solution (extractable solution) in which has been added solvent (e.g. isopropyl alcohol) destabilising polar emulsion or the water content of which is less than 40%, most preferably less than 25%. The low water content is advantageous at the end of the process when water residuals are removed from the extracted tall oil. The water content can be adjusted by using alkali-water solutions suitable of their content in the saponification.

The phases can be separated e.g. by decanting or centrifuging, whereby the results are a "light" organic extraction phase, which mainly contains extraction solvent and unsaponified material i.e. neutral components, and a "heavy" phase, extracted soap phase, which mainly contains the salts of fatty and resin acids. It is also probable that the greatest part of so-called pitch components are removed during the extraction stage.

The extraction temperatures are chosen based on the extraction solvent used i.e. the solvent cannot boil during extraction. It is advisable to keep the extraction temperature as low as possible, e.g. below 40° C., because then stable emulsions are not easily formed i.e. the soap and solvent phases differ adequately well from each other. The ratio of the extraction solvent to the soap solution can vary between 0.5:1-20:1. However, most advantageously it is 5:1. The extraction time is 0.5-4 hours.

Crude tall oil has to be restored from soap form back to oil. This is done by boiling saponified tall oil in acid solution (inorganic or organic acid). The best results are obtained with mineral acid solutions, such as sulphuric acid. A disadvantage of sulphuric acid is the unpleasant odour it causes. When wishing to affect the odour characteristics of the end-product, e.g. hydrochloric acid or phosphoric acid having a weaker odour can be used as the alternative of sulphuric acid.

During acid boiling, usually two phases are separated: an oil phase which includes fatty acids and resin acids and solvent residue (and also a little neutral components) and a water phase (saline solution) which includes sodium sulphate (if saponified with lye and acidified in sulphuric acid boiling) and only small amounts of fatty and resin acids. Of extracted tall oil, it is possible to finally remove solvent and water residues e.g. by evaporating the solution in normal pressure or vacuum. The solvent can be returned to the process after cleansing operations.

After such a process, the ratio of neutral components in the tall oil is less than 2 wt %. The result can be improved by distilling neutral components e.g. in falling-film evaporators, thin-film evaporators or fractionating columns.

Alternatively, the removal of neutral components in the crude tall oil can be done by distilling. Distilling the crude tall oil so that the components (fatty acids, resin acids and neutral components) contained by tall oil are separated is based on the different boiling points of tall oil components.

Possible distilling ways are e.g. azeotropic distillation, dry distillation, extraction distillation, fraction distillation, vacuum distillation, steam distillation and reactive distillation. Suitable columns are e.g. fractionating columns which can also be packed. Other possible apparatuses used in distilling are different evaporators, such as thin-layer evaporators.

Separating all neutral components by distilling directly from crude tall oil or melted crude tall oil soap is difficult, because a great number of neutral components are low-boiling compounds which are distilled along with fatty and resin acids, especially fatty acids. Due to this, in such distilling of neutral components, in which the aim is the complete removal of neutral components, several distillation stages have to be used. However in manufacturing wood preservative according to the invention, there is usually no need for more than one or two distillation stages, because the aim of manufacturing wood preservative according to the invention is to remove from crude tall oil only harmful neutral components contained by it, such as fatty alcohols and/or steroids, which are e.g. sitosterol and sitostanol.

The temperature ranges for distilling are usually extremely large and they are dependent on the apparatus and pressure used. Roughly, the most suitable temperature range is defined as about 150-400° C. The pressure should be clearly below air pressure. Usually it is advantageous if as high as possible underpressure can be used in distilling.

In the distillation of crude tall oil occurring in many stages, columns or other distillation apparatuses are connected in series for obtaining a cleaner end-product. At the first stage of distilling, usually fatty acids and low-boiling neutral components (about 150-250° C., underpressure) are the first to evaporate i.e. the temperature is kept below the boiling point of resin acids. Also higher temperatures can be used at the first stage, but then usually the amount of pitch increases and the amount of clean end-products decreases. Evaporated fatty acids are cooled in a cooler (50-180° C.) and, if required, processed further i.e. cleaning is continued by distilling at the next stages in specific conditions. The resin acids and other components remaining from the first stage are conveyed to the next cleaning/distillation stage in which they are distilled e.g. in about 300° C. in underpressure. The aim is to remove fatty acids and neutral components remaining in the mixture. The resin acids can be processed further, if desired, i.e. distilling or other cleaning measures can be continued in more specific conditions.

Pitch components are usually separated from the process after the first or second stage of distilling, as the material in question is complex. The components of pitch are created either in tall oil during distilling in high temperatures (over 300° C.) or are components contained by crude tall oil being of high-molar-mass and boiling only in very high temperatures. Component groups occurring in pitch are fatty and resin acids, esters of fatty acids, esters of resin acids, dimerised acids and neutral components (esters are formed e.g. when resin and fatty acids react with the alcohol groups of neutral components).

As mentioned above, also combinations of above-mentioned methods can be used for removing harmful neutral components. After removing neutral components, in the wood preservative can be inserted different additives, such as e.g. copper, boron, iron, chrome and/or suitable solvent for making the wood preservative to as suitable as possible form of its viscosity and other characteristics affecting usability.

In an embodiment, wood preservative was manufactured of tall oil by distilling. The distillation process was two-stage, whereby there were less distillation stages and the manufacture of the wood preservative was considerably simpler and more cost-effective than e.g. the manufacture of recently known wood preservatives manufactured of fatty and resin acids by mixing. In wood preservative manufactured in this way, there are typically 50-70 wt % of fatty acids, 20-50 wt % of resin acids and 0.1-4 wt % of neutral components. In such wood preservative, due to the small number of distillation stages, there are 0-1 wt % of pitch components, 0-0.2 wt % of monoterpenes, 0-1% of diterpenes and 0-0.3% of phenols. Furthermore in such wood preservative, there can also be about 0-1 wt % of other unknown blend components. Due to these remaining "impurities," the consistency of such wood preservative is considerably more versatile and thus usually better from the viewpoint of wood protection than in those known wood preservatives based on crude tall oil which are usually manufactured by mixing pure fatty and resin acids together.

The invention is not limited to the described advantageous embodiments, but it can vary within the scope of the inventive idea presented in the claims.

The invention claimed is:
1. Wood preservative, which wood preservative contains vegetable oils processed of crude tall oil, wherein the wood preservative is vegetable oil which is manufactured of crude tall oil by distilling from the crude tall oil neutral components; compounds causing esterification reactions and/or compounds acting as breeding ground and nutriment for rot fungi, and the wood preservative contains 50-70 wt % of fatty acids, 20-50 wt % of resin acids and 0.1-4 wt % of neutral components.

2. Wood preservative according to claim 1, wherein the wood preservative contains about 2 wt % of neutral components.

3. Wood preservative according to claim 1, wherein the wood preservative contains copper, boron, iron and/or chrome.

4. Wood preservative according to claim 1, wherein the crude tall oil has fatty alcohols and/or steroids distilled from the crude tall oil.

5. Wood preservative according to claim 1, wherein the crude tall oil has sitosterol and/or sitostanol distilled from the crude tall oil.

6. A method for manufacturing wood preservative, in which method, wood preservative is manufactured of vegetable oils contained by crude tall oil by distilling neutral components from the crude tall oil, from which are removed compounds causing esterification reaction and/or compounds acting as breeding ground and nutriment for rot fungi, and that the wood preservative contains 50-70 wt % of fatty acids, 20-50 wt % of resin acids and 0.1-4 wt % of neutral components.

7. The method of claim 6 where the removed compounds comprise fatty alcohol and/or steroid.

8. The method of claim 7 where the removed compounds comprise sitosterol and/or sitostanol.

* * * * *